(12) United States Patent
Huber et al.

(10) Patent No.: US 11,918,398 B2
(45) Date of Patent: Mar. 5, 2024

(54) ANALYSIS METHOD AND ANALYSIS UNIT FOR DETERMINING RADIOLOGICAL RESULT DATA

(71) Applicant: Siemens Healthcare GmbH, Erlangen (DE)

(72) Inventors: Peter Huber, Windsbach (DE); Bernhard Krauss, Burgthann (DE); Sebastian Schmidt, Weisendorf (DE); Bernhard Schmidt, Fuerth (DE)

(73) Assignee: SIEMENS HEALTHINEERS AG, Erlangen (DE)

( * ) Notice: Subject to any disclaimer, the term of this patent is extended or adjusted under 35 U.S.C. 154(b) by 831 days.

(21) Appl. No.: 16/358,790

(22) Filed: Mar. 20, 2019

(65) Prior Publication Data

US 2019/0298288 A1    Oct. 3, 2019

(30) Foreign Application Priority Data

Mar. 29, 2018 (EP) ..................................... 18165007

(51) Int. Cl.
*A61B 6/00* (2006.01)
*A61B 5/00* (2006.01)
(Continued)

(52) U.S. Cl.
CPC ............ *A61B 6/482* (2013.01); *A61B 5/7267* (2013.01); *A61B 6/032* (2013.01); *A61B 6/4241* (2013.01);
(Continued)

(58) Field of Classification Search
CPC ...................................................... A61B 6/482
See application file for complete search history.

(56) References Cited

U.S. PATENT DOCUMENTS 6,422,751 B1    7/2002  Aufrichtig et al.
2004/0252873 A1*  12/2004  Avinash ................ G06T 7/0012
                                                                 382/132
(Continued)

FOREIGN PATENT DOCUMENTS

CN    101229063 A    7/2008
CN    101292877 A    10/2008
(Continued)

OTHER PUBLICATIONS

Stackoverflow "Neural networks—input values" Mar. 16, 2009; pp. 1-4 // https://stackoverflow.com/questions/652530/neural-networksinput-values.

(Continued)

*Primary Examiner* — Bill Thomson
*Assistant Examiner* — Aminah Asghar
(74) *Attorney, Agent, or Firm* — Harness, Dickey & Pierce, P.L.C.

(57) ABSTRACT

An analysis method is for automatically determining radiological result data from radiology data sets. In an embodiment, the method includes provisioning a first radiology data set at least based on X-ray data of a first X-ray energy spectrum; provisioning at least one second radiology data set at least based on X-ray data of a second X-ray energy spectrum; provisioning an analysis unit including a neural network, to analyze radiology data sets including an input layer with a plurality of cells, a number of intermediate layers and an output layer representing a radiological result; analyzing the first radiology data set and the at least one second radiology data set, at least subsets of the first radiology data set and the at least one second radiology data set being assigned to different cells of the input layer for joint processing in the neural network; and acquiring result data on the output layer.

21 Claims, 3 Drawing Sheets

(51) Int. Cl.
*A61B 6/03* (2006.01)
*G06N 3/04* (2023.01)
*G06N 3/045* (2023.01)
*G06N 3/08* (2023.01)
*G06T 7/00* (2017.01)
*G06N 3/044* (2023.01)

(52) U.S. Cl.
CPC ............ *A61B 6/54* (2013.01); *G06N 3/04* (2013.01); *G06N 3/045* (2023.01); *G06N 3/08* (2013.01); *G06T 7/0012* (2013.01); *G06N 3/044* (2023.01); *G06T 2207/10081* (2013.01)

(56) References Cited

U.S. PATENT DOCUMENTS

| | | | |
|---|---|---|---|
| 2004/0264626 A1* | 12/2004 | Besson | A61B 6/563 378/4 |
| 2005/0169428 A1* | 8/2005 | Hardesty | A61B 6/542 378/110 |
| 2008/0144764 A1 | 6/2008 | Nishide et al. | |
| 2008/0212853 A1* | 9/2008 | Lin | G06T 7/11 382/128 |
| 2008/0317196 A1 | 12/2008 | Imai et al. | |
| 2011/0194668 A1 | 8/2011 | Kanno | |
| 2013/0342577 A1* | 12/2013 | Wang | A61B 6/482 345/634 |
| 2014/0140479 A1* | 5/2014 | Wang | A61B 6/5205 378/62 |
| 2014/0243579 A1* | 8/2014 | Roeske | A61B 6/485 600/1 |
| 2014/0270440 A1* | 9/2014 | Inglese | A61B 6/5205 382/131 |
| 2015/0371378 A1 | 12/2015 | Schmidt et al. | |
| 2016/0128666 A1 | 5/2016 | Grasruck et al. | |
| 2016/0174902 A1* | 6/2016 | Georgescu | G06T 7/0012 600/408 |
| 2016/0302751 A1* | 10/2016 | Grant | A61B 6/50 |
| 2016/0325040 A1 | 11/2016 | Flohr et al. | |
| 2016/0364889 A1 | 12/2016 | Raupach | |
| 2017/0046616 A1 | 2/2017 | Socher et al. | |
| 2017/0046839 A1 | 2/2017 | Buckler et al. | |
| 2017/0245816 A1 | 8/2017 | Flohr et al. | |
| 2017/0258412 A1* | 9/2017 | Daerr | A61B 6/06 |
| 2018/0042565 A1* | 2/2018 | Wilson | A61B 6/504 |
| 2018/0061059 A1* | 3/2018 | Xu | G06T 7/11 |
| 2018/0315190 A1* | 11/2018 | Sasagawa | G06N 3/08 |
| 2019/0038238 A1* | 2/2019 | Ray | A61B 6/4007 |
| 2019/0236774 A1* | 8/2019 | Gros | G16H 50/20 |
| 2019/0269384 A1* | 9/2019 | Lundberg | A61B 8/585 |
| 2019/0328348 A1* | 10/2019 | De Man | A61B 6/5205 |

FOREIGN PATENT DOCUMENTS

| | | |
|---|---|---|
| CN | 102215754 A | 10/2011 |
| CN | 105117611 A | 12/2015 |
| CN | 105581807 A | 5/2016 |
| CN | 106108928 A | 11/2016 |
| CN | 106251295 A | 12/2016 |
| CN | 106408522 A | 2/2017 |
| CN | 107133995 A | 9/2017 |
| JP | H07287330 A | 10/1995 |
| JP | 2000065943 A | 3/2000 |
| WO | WO 2017031088 A1 | 2/2017 |

OTHER PUBLICATIONS

StackExchange "Neural network—binary vs discrete / continuous input" Jun. 21, 2015; pp. 1-4 // https://stats.stackexchange.com/questions/157985/neural-network-binaryvs-discrete-continuous-input?answertab=oldest#tab-top.

Fechner, Thomas et al: "Learning target masks in infrared linescan imagery"; Proceedings of SPIE; Apr. 4, 1997; Downloaded From: https://www.spiedigitallibrary.org/conference-proceedings-of-spie an Aug. 29, 2018 Terms of Use: https://www.spiedigitallibrary.org/terms-of-use;;.

Tachibana Rie et al: "Deep learning for electronic cleansing in dual-energy CT colonography"; Progress in Biomedical Optics and Imaging; SPIE—International Society for Optical Engineering, Bellingham, WA, US; vol. 9785, Mar. 24, 2016 (Mar. 24, 2016), pp. 97851M-1-97851M-7; XP060070491; ISSN: 1605-7422; DOI: 10.1117/12.2216446; ISBN: 978-1-5106-0027-0.

Rogers Thomas W. et al: "A deep learning framework for the automated inspection of complex dual-energy x-ray cargo imagery"; SPIE Defense and Security Symposium; Mar. 16-20, 2008; Orlando, Florida, United States, SPIE, US; vol. 10187,; May 2017 (May 2017), pp. 101870L-1-101870L-12, XP060089791; ISSN: 0277-786X; DOI: 10.1117/12.2262662; ISBN: 978-1-5106-1723-0; 2017.

Woo-Jin Lee et al: "Material depth reconstruction method of multi-energy X-ray images using neural network"; in : Engineering in Medicine and Biology Society (EMBC); 2013 34th Annual International Conference of the IEEE, IEEE, Aug. 28, 2012 (Aug. 28, 2012); San Diego, US; pp. 1514-1517; XP032463214; ISSN: 1557-170X, D01: 10.1109/EMBC.2012.6346229; 2012.

Chuqing Feng et al.: "A multi-energy material decomposition method for spectral CT using neural network"; Medical Imaging 2018: Physics of Medical Imaging; Mar. 9, 2018 (Mar. 9, 2018), vol. 10573, pp. 105734J-1-105734J-8; XP55481989; DOI: 10.1117/12.2294611; ISBN: 978-1-5106-1636-3; 2018.

Alirezaie, J. et al: "Multi-spectral magnetic resonance image segmentation using LVQ neural networks"; Oct. 22, 1995.

Ozkan M. et al: "Multispectral magnetic resonance image segmentation using neural networks"; Jun. 17, 1990.

Iqbal Sajid et al: "Brain tumor segmentation in multi-spectral MRI using convolutional neural networks (CNN)", 2018 Wiley Periodicals, Inc., Microspy research technique. p. 419-427, wileyonlinelibrary.com/journal/jemt, 0DOI: 10.1002/jemt.22994, (Year 2018).

* cited by examiner

ANALYSIS METHOD AND ANALYSIS UNIT FOR DETERMINING RADIOLOGICAL RESULT DATA

PRIORITY STATEMENT

The present application hereby claims priority under 35 U.S.C. § 119 to European patent application number EP18165007.8 filed Mar. 29, 2018, the entire contents of which are hereby incorporated herein by reference.

FIELD

Embodiments of the invention generally relate to an analysis method and an analysis unit and/or a neural network for automatically determining radiological result data from radiology data sets, in particular, spectral computed tomography data, and a corresponding control device for controlling an X-ray system, a corresponding diagnostic workstation for coupling to an X-ray system, and a corresponding medical imaging system.

BACKGROUND

In radiological imaging, the effective analysis and processing of radiological images is essential. Methods based on machine learning are increasingly being used for this purpose. Using such methods, objects in images, for example, pathological changes, can be automatically detected and displayed for the diagnosing physician.

Methods used frequently are based on neural networks, and/or such methods are based on simulated neurons. Examples of such neural networks are Deep Learning or Convolutional Neural Networks (CNN). Neural networks usually comprise an input layer (first layer), into which the data for processing is input, a number of intermediate layers which are used for processing and an output layer which provides the result of the processing.

For example, in the input layer of the network the pixels (in a two-dimensional measurement) and/or voxels (in a three-dimensional measurement) are assigned to the cells of the layer ("neurons"), so that each neuron receives the signal value of the assigned pixel as an input variable. The output layer then contains as many neurons as different results of the classification are possible.

Increasingly, in the context of radiology technology, in particular with regard to computed tomography ("CT"), recording methods employing a plurality of recording energies are used. Recently, some devices have even used spectral detectors which no longer generate only one signal value per pixel but can also distinguish the spectral energy of the incoming photons.

However, optimum use is not currently being made of this recording method with a plurality of recording energies and/or an energy spectrum, constituting a serious disadvantage in view of the potential of such recordings. As a rule, conventional CT images with only one signal value per pixel are reconstructed from spectral CT data, wherein the different spectral components are weighted differently in order to generate a particular image impression (for example, accentuation of a contrast agent which has a specific absorption spectrum).

SUMMARY

At least one embodiment of the present invention provides an alternative, more convenient analysis method, an analysis unit and/or a neural network for automatically determining radiological result data from radiology data sets, and a corresponding control device for controlling an X-ray system, a corresponding diagnostic workstation for coupling to an X-ray system, and a corresponding medical imaging system with which the disadvantages described above can be avoided.

At least one embodiment is directed to an analysis method, an analysis unit, a neural network, a control device, a diagnostic workstation and a medical imaging system as claimed.

The analysis method according to at least one embodiment of the invention and/or the analysis unit according to at least one embodiment of the invention serves to automatically determine radiological result data on the basis of and/or from radiology data sets.

The analysis method according to at least one embodiment of the invention, for automatically determining radiological result data from radiology data sets, comprises:

provisioning a first radiology data set at least based on X-ray data of a first X-ray energy spectrum;

provisioning at least one second radiology data set at least based on X-ray data of a second X-ray energy spectrum;

provisioning an analysis unit including a neural network, designed to analyze radiology data sets including an input layer with a plurality of cells, a number of intermediate layers and an output layer representing a radiological result;

analyzing, via the neural network, the first radiology data set and the at least one second radiology data set, at least subsets of the first radiology data set and the at least one second radiology data set being assigned to different cells of the input layer for joint processing in the neural network; and acquiring result data on the output layer.

An analysis unit according to at least one embodiment of the invention accordingly comprises:

A data interface for acquiring at least two radiology data sets. The first radiology data set is based, as already explained in detail above, at least on X-ray data of a first X-ray energy spectrum, the second radiology data set is at least based on X-ray data of a second X-ray energy spectrum. As mentioned, further radiology data sets can be acquired.

A neural network designed to analyze radiology data sets, which comprises an input layer, a number of intermediate layers and an output layer. The above applies to the layers.

The analysis unit according to at least one embodiment of the invention is designed to analyze the first radiology data set and at least the second radiology data set (and if applicable, further radiology data sets) via the neural network. For this purpose, subsets (see above) of the first radiology data set and at least the second radiology data set are assigned to the cells of the input layer for joint processing.

In addition, the analysis unit is designed to acquire result data on the output layer.

A neural network according to at least one embodiment of the invention comprises an input layer with a plurality of cells, a number of intermediate layers and an output layer which represents a radiological result. It is designed such that subsets of a first radiology data set at least based on X-ray data of a first X-ray energy spectrum and of at least a second radiology data set at least based on X-ray data of a second X-ray energy spectrum are assigned to the cells of the input layer for joint processing. In addition, the neural network is designed to generate radiological result data and to make it available on the output layer.

A control device according to at least one embodiment of the invention for controlling an X-ray system, in particular a computed tomography system, comprises an analysis unit according to at least one embodiment of the invention and/or it is designed to carry out an analysis method according to at least one embodiment of the invention.

A diagnostic workstation according to at least one embodiment of the invention is designed for coupling to an X-ray system, in particular, to a computed tomography system. The diagnostic workstation comprises an analysis unit according to at least one embodiment of the invention and/or it is designed to carry out an analysis method according to at least one embodiment of the invention. The diagnostic workstation can be integrated into an X-ray system, for example, into its control device. In practice, however, it is more often the case that it is present in the form of a powerful computing device in the context of a Radiology Information System ("RIS") or a Picture Archiving and Communication System ("PACS").

A medical imaging system according to at least one embodiment of the invention comprises an X-ray system and an analysis unit according to at least one embodiment of the invention. The analysis unit is preferably present in the medical imaging system in the form of a diagnostic workstation according to at least one embodiment of the invention and/or a control device according to at least one embodiment of the invention. The control device can also be part of the X-ray system.

The majority of the aforementioned components which are necessary for the embodiments of the invention can be implemented wholly or partially in the form of software modules in a processor of a corresponding appliance and/or control device. A largely software-based implementation has the advantage that even previously used appliances and/or control devices can be retrofitted in a simple manner by a software update to operate in the manner according to embodiments of the invention.

In this respect, at least one embodiment is also directed to a corresponding computer program product with a computer program which can be loaded directly into a computer system and/or a storage device of a control device of an X-ray system, with program segments to perform all the steps of at least one embodiment of the method according to the invention when the program is executed in the computer system and/or the control device. In addition to the computer program, such a computer program product may, if required, comprise additional components such as, for example, documentation and/or additional components and hardware components such as, for example, hardware keys (dongles, etc.) for use of the software.

For transport to the computer system and/or the control device and/or for storage on or in the computer system and/or the control device, a computer-readable medium, for example, a memory stick, a hard disk or another transportable or permanently installable data carrier can be used on which the program segments of the computer program which are readable and executable by a computer system and/or a computer unit of the control device are stored. The computer unit can, for example, have one or a plurality of interacting microprocessors or the like for this purpose.

Further, particularly advantageous embodiments and developments of the invention will emerge from the claims and the following description, wherein the claims of a claim category can also be developed analogously to the claims and description parts of another claim category and in particular, individual features of different example embodiments and/or variants can also be combined to form new example embodiments and/or variants.

BRIEF DESCRIPTION OF THE DRAWINGS

The invention is explained in more detail once again hereinafter with reference to the accompanying figures on the basis of example embodiments. The same components are provided with identical reference characters in the various figures. The figures are not usually to scale. In the figures.

DETAILED DESCRIPTION OF THE EXAMPLE EMBODIMENTS

Figure 1:
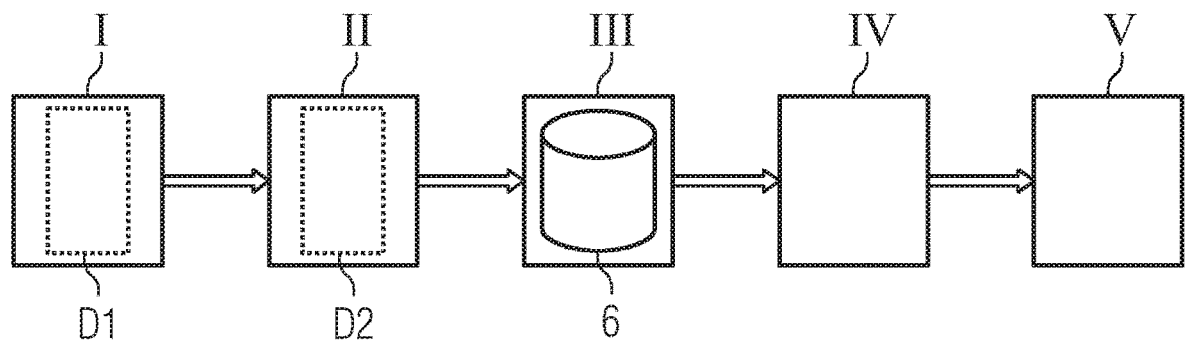
FIG. 1 shows a flow chart for a possible sequence of an analysis method according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

The radiology data sets are preferably CT data sets, that is to say, generated via a computed tomography system. However, they can also be generated on another device which operates with X-rays, for example, a simple X-ray fluoroscopy device, a mammography device, an angiograph, etc.

Hereinafter, a radiology data set can be understood to mean, on the one hand, the raw data set directly measured on the device, for example, the computed tomography system. Likewise, however, this can also be understood to mean an image data set reconstructed on the basis of this raw data set. This depends only on whether the raw data is to be used directly in the neural network or with the image data.

These radiology data sets represent different X-ray images with a plurality of X-ray energy spectra. It should be noted that in reality there is always a certain energy width in the case of an X-ray image, even if the "X-ray energy spectrum" is narrow-banded. However, the recording is generally designated with a value for a discrete X-ray energy, for example with the applied voltage at the X-ray source.

The X-ray energy spectrum is determined, for example, by the adjustment of the X-ray source and/or detector or by a selection of measurement data of the detector, if the latter can operate in an energy-selective manner. Insofar as "X-ray data of an X-ray energy spectrum" is mentioned, this is therefore understood to mean measurement data of an X-ray system, for example, a computed tomography system, which has been provided with the corresponding X-ray energy spectrum.

In this case, preference is given to "spectral" radiology data sets recorded with an X-ray system that emits an X-ray beam with a broad X-ray energy spectrum, wherein the detector system is designed such that it no longer generates only one signal value per pixel, but can also distinguish the spectral energy of the incoming photons, in other words, is energy-selective. Instead of a single gray value per pixel and/or measurement point, spectral radiology data sets may therefore have many values which reproduce recording values over a broad spectrum. In principle, however, such spectral radiology data sets can also be generated by combining X-ray data of different X-ray energy spectra, regardless of whether the X-ray data of the different X-ray energy spectra was recorded in a measurement process, for example with an energy-selective detector, or in succession.

The analysis method according to at least one embodiment of the invention comprises: The provision of a first radiology data set. The first radiology data set is at least based on X-ray data of a first X-ray energy spectrum. The first radiology data set was therefore recorded during the first X-ray energy.

The analysis method according to at least one embodiment of the invention further comprises the provision of at least a second radiology data set. The second radiology data set is at least based on X-ray data of a second X-ray energy spectrum which differs from the first X-ray energy spectrum. In this case, however, two X-ray energy spectra need not necessarily always be completely disjoint, even if this is quite advantageous for most applications. Nevertheless, it can be advantageous for some special applications if the first and the second X-ray energy spectrum overlap, or one X-ray energy spectrum is contained in the other X-ray energy spectrum.

The term "at least" means that further radiology data sets can be provided which have been recorded with further X-ray energy spectra, wherein the same applies to these further X-ray energy spectra as to the second X-ray energy spectrum: the different X-ray energy spectra should not be identical to one another but can optionally comprise parts of the other X-ray energy spectra. For example, in the case of more than two radiology data sets, one of the radiology data sets can also represent the (possibly normalized) sum of a number of the other radiology data sets.

The method is preferably designed to operate with at least three, four, five or six radiology data sets.

The analysis method according to at least one embodiment of the invention further comprises: The provision of an analysis unit.

This analysis unit comprises a neural network designed to analyze radiology data sets, and in particular, (pre)trained, which comprises an input layer, a number of intermediate layers and an output layer. The input layer has a plurality of cells which are also referred to as "neurons" in many neural networks. The output layer represents a radiological result, for example, a series of possible findings, preferably together with the probability that these findings are present in the recordings.

In the analysis step, the first radiology data set and at least the second radiology data set are analyzed via the neural network. For this purpose, subsets of the first radiology data set record and at least of the second radiology data set are assigned to the cells of the input layer for joint processing. These subsets are preferably a group of pixel values (for example, a single or a plurality of pixels and/or voxels), a group of raw data values (whereby a single raw data value can also be meant) and/or a quantity of the image information. The neural network is designed to generate result data in the output layer from the data in the input layer.

According to at least one embodiment of the invention, a special assignment of the cells of the input layer (input layer) to the input data or to the detector of the X-ray recording system (measuring device and signal processing) is therefore proposed. The processing layers (intermediate layers or "hidden layers") between the input layer and the output layer can in principle be selected arbitrarily, but preferably "deep" networks are used, i.e. with more than one intermediate layer. The output layer corresponds to radiological "properties" which can be derived from the image information—or, if applicable, also directly from the raw data. This can be, for example, a diagnosis (lung cancer: Yes/No), morphological properties (presence of pulmonary nodules) or quantitative properties (volume of pulmonary nodules).

Training the neural network modifies the weightings of the connections in the architecture of the network. In this case, neural networks are usually trained in such a way that pairs of input data and (valid) result data matching them are used. In the present case, these would be pairs of spectral radiology data sets (for example, CT data sets) and radiological results, for example, findings, diagnoses or measurements which have been generated manually by persons skilled in the art or also in an automated manner using other methods. Synthetic pairs may also be used, for example, by randomly generating nodules of known diameter in radiology data sets and then using them for training. The training can then take place using known methods, for example, backpropagation.

It is pointed out here that also in the context of the analysis, the neural network can always be further trained and thus improved, for example, by verifying the result data.

After the processing of the radiology data sets by the neural network, the result data of the processing is present, as mentioned, on the output layer and can be acquired there.

An analysis unit according to at least one embodiment of the invention accordingly comprises:

A data interface for acquiring at least two radiology data sets. The first radiology data set is based, as already explained in detail above, at least on X-ray data of a first X-ray energy spectrum, the second radiology data set is at least based on X-ray data of a second X-ray energy spectrum. As mentioned, further radiology data sets can be acquired.

A neural network designed to analyze radiology data sets, which comprises an input layer, a number of intermediate layers and an output layer. The above applies to the layers.

The analysis unit according to at least one embodiment of the invention is designed to analyze the first radiology data set and at least the second radiology data set (and if applicable, further radiology data sets) via the neural network. For this purpose, subsets (see above) of the first radiology data set and at least the second radiology data set are assigned to the cells of the input layer for joint processing.

In addition, the analysis unit is designed to acquire result data on the output layer.

A neural network according to at least one embodiment of the invention comprises an input layer with a plurality of cells, a number of intermediate layers and an output layer which represents a radiological result. It is designed such that subsets of a first radiology data set at least based on X-ray data of a first X-ray energy spectrum and of at least a second radiology data set at least based on X-ray data of a second X-ray energy spectrum are assigned to the cells of the input layer for joint processing. In addition, the neural network is designed to generate radiological result data and to make it available on the output layer.

A control device according to at least one embodiment of the invention for controlling an X-ray system, in particular a computed tomography system, comprises an analysis unit according to at least one embodiment of the invention and/or it is designed to carry out an analysis method according to at least one embodiment of the invention.

A diagnostic workstation according to at least one embodiment of the invention is designed for coupling to an X-ray system, in particular, to a computed tomography system. The diagnostic workstation comprises an analysis unit according to at least one embodiment of the invention and/or it is designed to carry out an analysis method according to at least one embodiment of the invention. The diagnostic workstation can be integrated into an X-ray system, for example, into its control device. In practice, however, it is more often the case that it is present in the form of a powerful computing device in the context of a Radiology Information System ("RIS") or a Picture Archiving and Communication System ("PACS").

A medical imaging system according to at least one embodiment of the invention comprises an X-ray system and an analysis unit according to at least one embodiment of the invention. The analysis unit is preferably present in the medical imaging system in the form of a diagnostic workstation according to at least one embodiment of the invention and/or a control device according to at least one embodiment of the invention. The control device can also be part of the X-ray system.

The majority of the aforementioned components which are necessary for the embodiments of the invention can be implemented wholly or partially in the form of software modules in a processor of a corresponding appliance and/or control device. A largely software-based implementation has the advantage that even previously used appliances and/or control devices can be retrofitted in a simple manner by a software update to operate in the manner according to embodiments of the invention.

In this respect, at least one embodiment is also directed to a corresponding computer program product with a computer program which can be loaded directly into a computer system and/or a storage device of a control device of an X-ray system, with program segments to perform all the steps of at least one embodiment of the method according to the invention when the program is executed in the computer system and/or the control device. In addition to the computer program, such a computer program product may, if required, comprise additional components such as, for example, documentation and/or additional components and hardware components such as, for example, hardware keys (dongles, etc.) for use of the software.

For transport to the computer system and/or the control device and/or for storage on or in the computer system and/or the control device, a computer-readable medium, for example, a memory stick, a hard disk or another transportable or permanently installable data carrier can be used on which the program segments of the computer program which are readable and executable by a computer system and/or a computer unit of the control device are stored. The computer unit can, for example, have one or a plurality of interacting microprocessors or the like for this purpose.

Further, particularly advantageous embodiments and developments of the invention will emerge from the claims and the following description, wherein the claims of a claim category can also be developed analogously to the claims and description parts of another claim category and in particular, individual features of different example embodiments and/or variants can also be combined to form new example embodiments and/or variants.

Preferably, for analysis in each case exactly one pixel value or raw data value of the first radiology data set or the second radiology data set is assigned to a number of cells of the input layer, in particular to each cell. These cells are therefore not given a large block of data, but only the value of a pixel (or voxel) and/or a data value.

In this case, each individual pixel value and/or each individual raw data value of the radiology data sets is preferably assigned to a cell of the input layer. The respective recordings represented by the radiology data sets are therefore completely transferred to the network.

In principle, two-dimensional, three-dimensional or four-dimensional radiology data sets can be used, wherein four-dimensional radiology data sets comprise a plurality of three-dimensional radiology data sets of the same volume which have been obtained at different times. With the value n for the number of X-ray energy spectra, the coordinates x, y and z and the time t, the resulting array therefore has the format [n,x,y,z,t], wherein n,x,y must always be present. The proportions z and t can also be omitted if, for example, only two-dimensional cases are covered.

If, for example, n images are present as two-dimensional images with x·y pixels and if a pixel is assigned to each cell, wherein the n recordings with their entire image information are processed by the neural network, then the input layer contains n·x·y neurons. The number n is then also the number of spectral groups as the recordings all represent a non-identical recording energy. The values x and y are also the size of the image matrix of the reconstructed images in the direction of x and y. In an example case in which three-dimensional data of volume images is processed with the format x·y·z (and not as single layer images), n·x·y·z accordingly results for the number of cells in the input layer for processing of the voxels. Processing and/or assignment of the pixels takes place analogously for three and four-dimensional measurements and/or radiology data sets.

In a preferred variant, the method may comprise several stages. In an analysis step, only a part of the radiology data sets for analysis is analyzed. Another part of the radiology data sets for analysis is then analyzed in at least one further analysis step which preferably operates analogously to the preceding step. The radiology data sets are therefore analyzed, for example, segment-by-segment: partial image for partial image and/or sub-areas of the raw data are analyzed in succession. With this embodiment, it is possible to take the neural network over a number of radiology data sets, in particular, image data and/or image recordings, as a "Sliding Window", which can, for example, constitute an advantageous reduction in computational effort in the case of very large data volumes and an analysis with regard to small structures. For example, in this regard a relatively small neural network (for example, with a grid of 20·20) can "go" over the radiology data sets.

Preferably, the neural network comprises at least 2, preferably at least 5, in particular at least 20, intermediate layers. The advantage of this is that principles of "Deep Learning" can be employed.

In principle, however, embodiments of the invention are not restricted to a particular type of network. Preferred neural networks are Convolutional Neural Networks ("CNN") or Long-Term Short-Term Memory Networks ("LTSM"). LTSM networks are particularly advantageous if time-resolved (four-dimensional) data is to be used.

Preferably at least one of the radiology data sets provided is at least based on X-ray data of two different X-ray energy spectra, preferably on combination data of radiology data sets based on X-ray data of the different X-ray energy spectra. The relevant data is preferably combined in the form of a (in particular, weighted) sum and/or a difference and/or a quotient and/or a product, wherein a combination of these arithmetic operations is also preferred, for example, a sum together with a normalization.

Preferably, a whole X-ray data set is divided to provide the first radiology data set and the second radiology data set. This whole X-ray data set was measured with a third X-ray energy spectrum comprising the first X-ray energy spectrum and the second X-ray energy spectrum. This is preferably achieved by dividing raw data of a measurement with the third X-ray energy spectrum into different raw data sets and reconstructing different image data sets based on the different raw data sets. The whole X-ray data set may comprise, for example (if necessary, exclusively) raw data or a reconstructed image data set, depending on whether the analysis is to be based directly on the raw data or on the image data. A preferred analysis unit preferably comprises a dividing unit which is designed for such a division.

In a preferred medical imaging system, the X-ray system comprises an energy-resolving detector, particularly preferably a directly converting detector.

FIG. 1 shows a flow chart for a possible sequence of an analysis method according to an embodiment of the invention for automatically determining radiological result data based on radiology data sets D1, D2.

In step I, a first radiology data set D1 is made available based on X-ray data of a first X-ray energy spectrum E1.

In step II, a second radiology data set D2 is made available based on X-ray data of a second X-ray energy spectrum E2. The second radiology data set D2 (and if applicable, further radiology data sets D3, D4) may by all means be made available at the same time as the first radiology data set D1.

In step III, an analysis unit 6 according to an embodiment of the invention is made available.

In step IV, the first radiology data set D1 and the second radiology data set D2 are analyzed via the analysis unit 6. How this is preferably done is shown in more detail in FIGS. 2 and 3.

In step V, result data is acquired.

Hereinafter, for the sake of better understanding it is assumed, for example, that image data will be used, wherein, however, it would be just as easy to use raw data instead of the image data, i.e. the reconstruction step can then be omitted.

Likewise, hereinafter it is assumed that the measurements are computed tomography images, wherein as mentioned, however, the invention is not limited to computed tomography.

Figure 2:
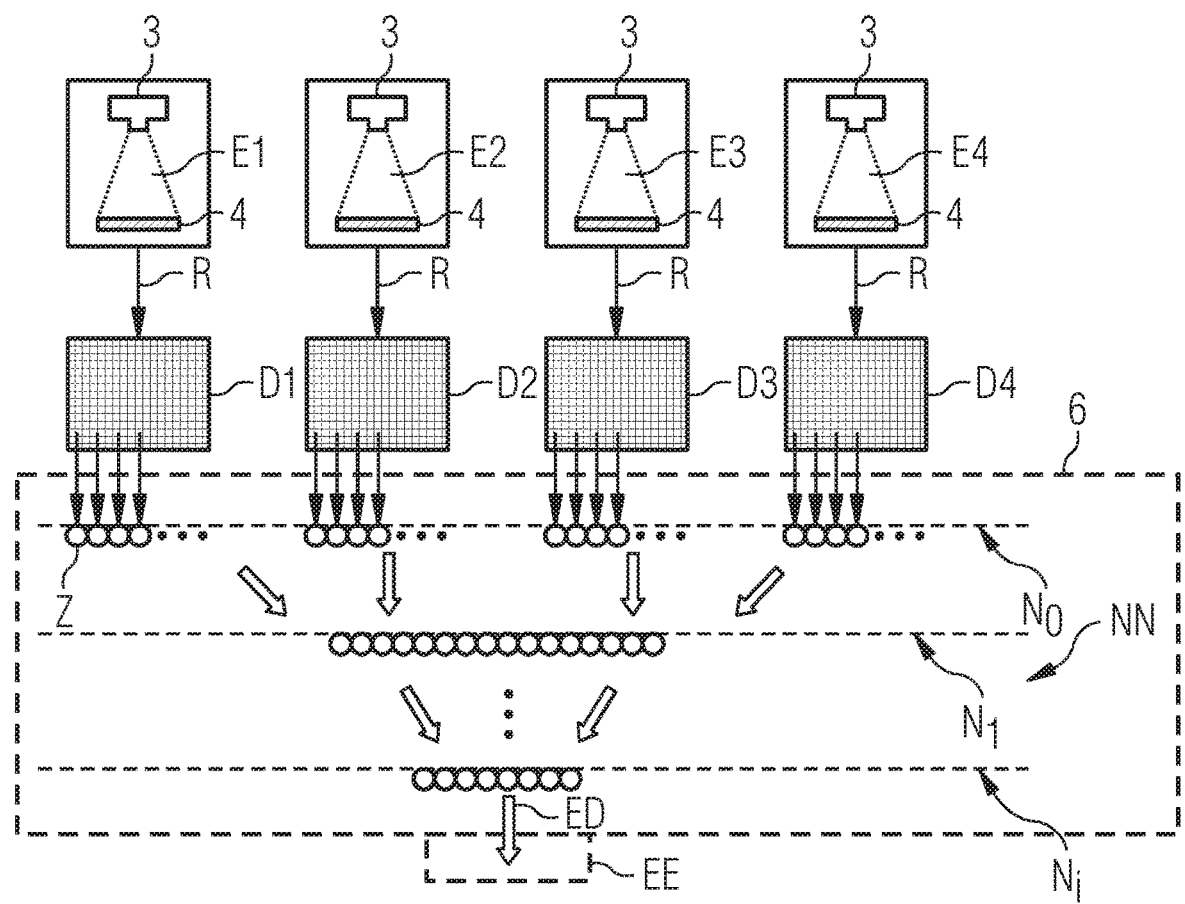
FIG. 2 shows a representation of an example embodiment for the division and analysis of radiology data sets.

FIG. 2 shows a representation of an example embodiment for analyzing—here as an example, four-radiology data sets D1, D2, D3, D4. Firstly, in this example four "separate" measurements and/or recordings take place via an X-ray source 3 and a detector 4, each with different X-ray energy spectra (E1, E2, E3, E4). These images can be produced simultaneously, for example with four pairs of X-ray sources 3 and detectors 4, or in succession (if applicable, with a single X-ray source which is operated with different acceleration voltages).

These measurements and/or images produce four radiology data sets D1, D2, D3, D4.

In this example, as mentioned, for reasons of better clarity the radiology data sets D1, D2, D3, D4 are available in the form of two-dimensional images with individual pixels which have been reconstructed from raw data of the individual images in a reconstruction method R. The format of these images could, for example, be assumed to be x-pixels wide and y-pixels high.

In this case, it is also possible that one of the radiology data sets D1, D2, D3, D4 (or a plurality) comprises data from two or more combined recordings with different X-ray energy spectra (E1, E2, E3, E4).

The radiology data sets D1, D2, D3, D4 are now provided according to the inventive method for processing by the analysis unit 6. This comprises a neural network NN designed for an analysis of radiology data sets, here in the form of image recordings B, which comprises an input layer NO with a plurality of cells Z, a number of intermediate layers N1 and an output layer Ni, which represents a radiological result. The number of intermediate layers would be i−1 here, with i a preferred number between 5 and 20.

For analysis of the radiology data sets D1, D2, D3, D4 via the neural network NN, individual pixels of the radiology data sets D1, D2, D3, D4 (which here correspond to the subsets of the radiology data sets D1, D2, D3, D4) are assigned to the cells Z (neurons) of the input layer NO for joint processing as shown. Here, the input layer NO contains 4·x·y cells Z (neurons) for the individual pixels of the four radiology data sets D1, D2, D3, D4.

After processing the radiology data records D1, D2, D3, D4, the result data ED can be acquired on the output layer Ni, for example accepted or read out by a result data unit EE. According to the type and the training of the neural network NN, this result data ED then indicates, for example, whether an abnormality is present in the images or not, if applicable, which type of abnormality and/or the extent.

Figure 3:
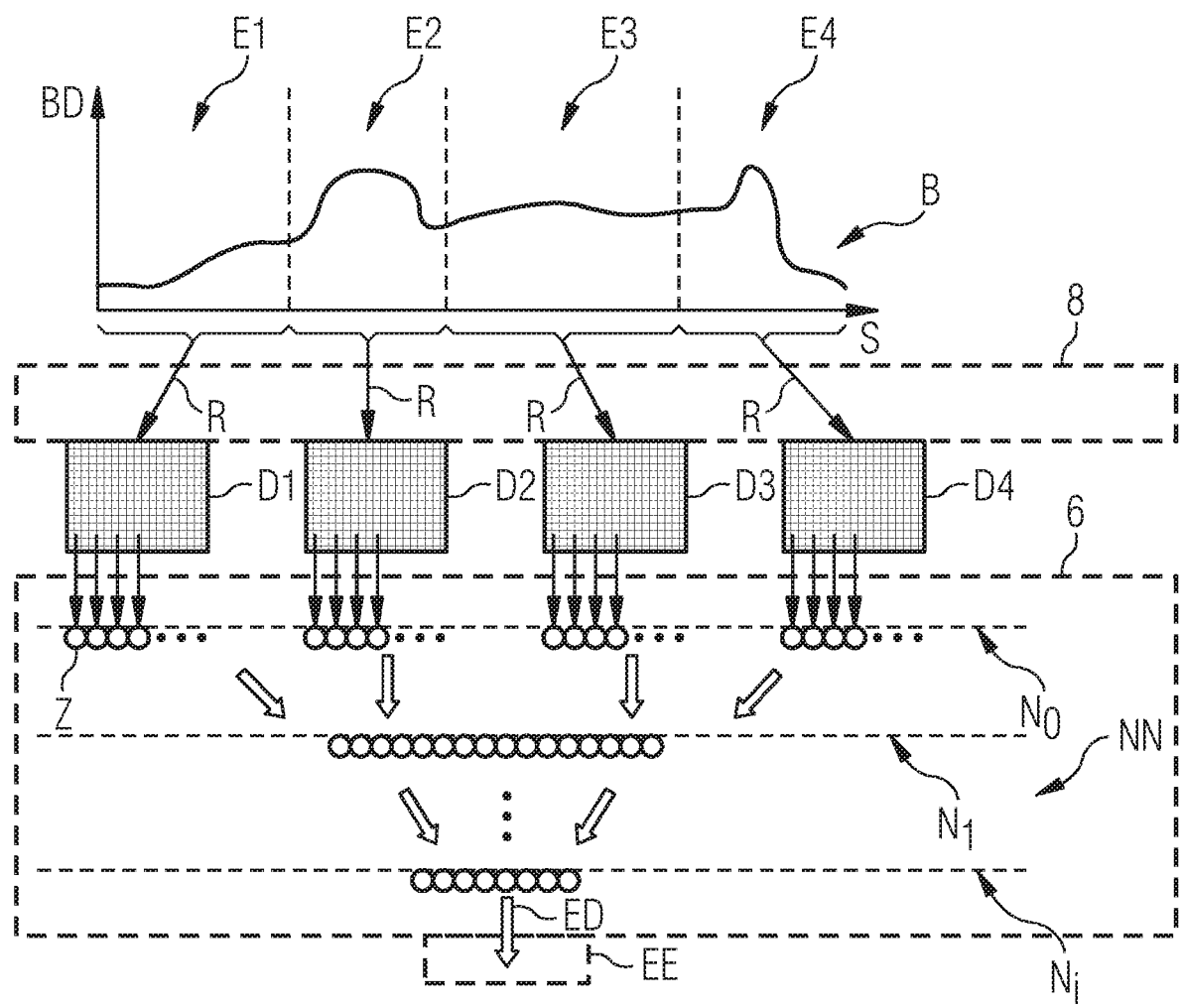
FIG. 3 shows a representation of a further example embodiment for the division and analysis of the radiology data sets.

FIG. 3 shows a representation of a particularly preferred example embodiment for analyzing the radiology data D1, D2, D3, D4. This figure is very similar to FIG. 2, at least as far as the analysis is concerned. Unlike FIG. 2, however, the radiology data sets D1, D2, D3, D4 are formed differently.

In this example embodiment only one recording and/or measurement was performed with an energy-resolving and/or "spectral" detector which can distinguish the spectral energy of the incoming photons. Thus, for pixels of this image recording B, a spectrum S of image data BD results (which, for example, can correspond to gray values for an energy). It is clear that in this case the X-ray radiation used must have a correspondingly broad energy spectrum.

The incoming signals on the detector (X-rays) are first classified in four predetermined X-ray energy spectra E1, E2, E3, E4 (which may also be referred to as "spectral regions" here) according to threshold values and selected as radiology data sets D1, D2, D3, D4 for individual images from this data. The four radiology data sets D1, D2, D3, D4 could, for example, have data on photons received from the detector 4 with an energy of 0 to 40 KeV (first radiology data set D1 based on the first X-ray energy spectrum and/or spectral range E1), 40 to 65 KeV (second radiology data set D2 based on the second X-ray energy spectrum and/or spectral range E2), 65 to 90 KeV (third radiology data set D3 based on the third X-ray energy spectrum and/or spectral range E3) and energies greater than 90 KeV (fourth radiology data set D4 based on the fourth X-ray energy spectrum and/or spectral range E4).

After processing the radiology data sets D1, D2, D3, D4, the result data ED can be detected on the output layer Ni, for example, again by way of a result data unit EE.

A specific clinical example would be a neural network NN, which can characterize kidney stones. Input data (radiology data sets D1, D2, D3, D4) are then, for example, four reconstructed (image) data sets, which each represent measurements in an X-ray energy spectrum E1, E2, E3, E4. Each voxel of each of the image data sets would then be assigned to a cell Z of the input layer E0.

Analogous to the example embodiment according to FIG. 3, the complete processing chain is as follows:

The detector first "sorts" the incoming raw data according to X-ray energy spectra E1, E2, E3, E4 during rotation (into its "bins"). This then produces a plurality of sinograms (according to X-ray energy spectra E1, E2, E3, E4) as raw data. From this, in turn, radiology data sets D1, D2, D3, D4 are reconstructed and these are fed into a neural network NN.

The input layer E0 could correspond to the number and structure of the data sets, the output layer Ni would have a classification "presence of a kidney stone" and "urate vs. calcium" (in extreme cases, only individual neurons).

This neural network NN would be sufficiently trained before the first analysis application. After completed training it is then able to detect and classify kidney stones, wherein spectral (kidney stone material) as well as morphological information (size, location, texture) is included.

To train the neural network NN, in this example data sets from patients P were used in which the presence the composition of the kidney stone is known, for example, because the kidney stone was recovered and chemically analyzed.

Hereinafter a further possible construction of an X-ray system 1 is described on which the method can be employed. The explanations assume that the X-ray system 1 is a computed tomography system 1. In principle, however, the method can also be used in other X-ray systems.

Figure 4:
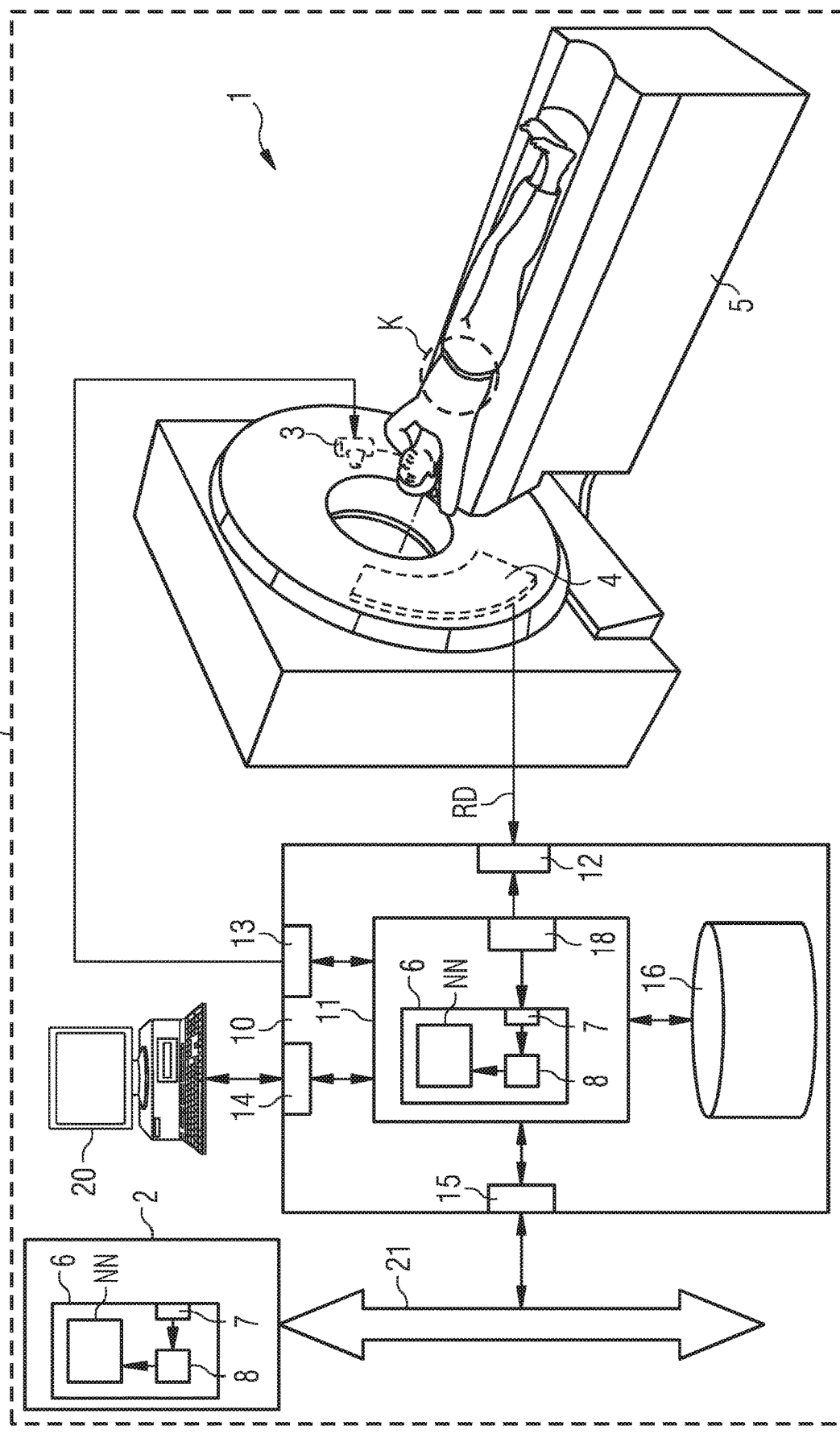
FIG. 4 shows a roughly schematic representation of an X-ray system with an example embodiment of a control device according to the invention and a diagnostic workstation for carrying out the method.

FIG. 4 shows a roughly diagrammatic view of a computed tomography system 1 with a control device 10 for performing the method according to the invention. The computed tomography system 1 has, in conventional fashion, a scanner with a gantry in which an X-ray source 3 rotates, which in each case irradiates a patient who is pushed via a couch 5 into a measuring area of the gantry so that the radiation impinges on a detector 4 opposite the X-ray source 3 respectively. It is expressly pointed out that the example embodiment according to FIG. 4 is only an example of a CT and the invention can also be used on any CT structures, for example, with a ring-shaped stationary X-ray detector and/or a plurality of X-ray sources.

Likewise, only the components which are essential or helpful for explaining the invention are shown in the control device 10. In principle, such CT systems and associated control devices are known to a person skilled in the art and therefore need not be described in detail.

In this example, the X-ray source 3 and the detector 4 are designed for a recording method which uses a plurality of recording energies. For example, the detector 4 can generate more than only one signal value per pixel, and thereby distinguish the spectral energy of the incoming photons. In another example embodiment, two or more X-ray sources 3 and detectors 4 could also be present which are designed for recordings with different respective energies.

A core component of the control device 10 here is a processor 11 on which various components in the form of software modules are realized. Furthermore, the control device 10 has a terminal interface 14 to which a terminal 20 is connected by way of which an operator can operate the control device 10 and thus the computed tomography system 1. A further interface 15 is a network interface for connection to a data bus 21 in order to establish a connection to an RIS and/or PACS. Via this bus 21, for example, radiology data D1, D2, D3, D4 can be sent to a diagnostic workstation 2.

The scanner can be controlled by the control device 10 via a control interface 13, i.e. for example, the rotation speed of the gantry, the displacement of the patient couch 5 and the X-ray source 3 are controlled themselves. The raw data RD is read out from the detector 4 via an acquisition interface 12. Furthermore, the control device 10 has a storage unit 16 in which, for example, various measurement protocols are stored.

An analysis unit 6 is implemented on the processor 11 as a software component. In this example, this analysis unit 6 receives reconstructed image data BD via a data interface 7 from an image data reconstruction unit 18 with which the desired image data BD is reconstructed from the raw data RD obtained via the data acquisition interface 12. However, this image data reconstruction unit 18 can also be omitted in other types of application and the analysis carried out directly with the raw data RD.

The analysis unit 6 further comprises a dividing unit 8 which is designed, after detecting spectral raw data RD or in this example, reconstructed image data BD based on X-ray data from at least two measurements with different X-ray energy spectra E1, E2, E3, E4 by the data interface 7, to create the individual radiology data sets D1, D2, D3, D4 by dividing the raw data RD or the image data BD according to their X-ray energy spectra E1, E2, E3, E4. Dividing the data into radiology data sets D1, D2, D3, D4 was described in more detail above in the description of FIGS. 2 and 3.

The analysis unit 6 also comprises a neural network NN designed, in particular, already trained, to analyze radiology data sets D1, D2, D3, D4, which comprises an input layer NO with a plurality of cells Z, a number of intermediate layers N1 and an output layer Ni which represents a radiological result (cf. FIGS. 2 and 3). The analysis unit is designed to analyze the radiology data provided via the neural network NN, as already described in more detail above.

The diagnostic workstation 2 is very similar to the control device 10 in design. It also comprises the analysis unit 6 described above. The diagnostic workstation 2 and the control device 10 may be present together as shown here (in which both comprise an analysis unit 6 according to the invention). However, the medical imaging system may also only have an analysis unit 6 according to the invention in one of these two components.

Finally, it is pointed out once again that the analysis method previously described in detail and the appliances and/or units and/or the computed tomography system 1 illustrated are only example embodiments which can be modified by a person skilled in the art in a variety of ways without departing from the scope of the invention. Moreover, the use of the indefinite article "a" and/or "an" does not preclude the features concerned also possibly being present multiple times. Likewise, the terms "unit" and "module" do not preclude the components concerned from consisting of a plurality of interacting component parts which may also be spatially distributed, if necessary.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An analysis method for automatically determining radiological result data from radiology data sets, the analysis method comprising:

provisioning a first radiology data set, the first radiology data set being at least based on X-ray data of a first X-ray energy spectrum;

provisioning at least one second radiology data set, the at least one second radiology data set being at least based on X-ray data of a second X-ray energy spectrum;

provisioning an analysis unit, the analysis unit including a neural network configured to analyze the first radiology data set and the at least one second radiology data set, the neural network including
an input layer with a plurality of cells, wherein a number of the plurality of cells of the input layer are each assigned only one pixel value or only one raw data value of the first radiology data set or the at least one second radiology data set,
a number of intermediate layers, and
an output layer representing the radiological result data;

dividing the first radiology data set into a first subset and a second subset;

dividing the at least one second radiology data set into a first subset and a second subset;

analyzing, via the neural network in a first analyzing step, the first subset of the first radiology data set and the first subset of the at least one second radiology data set, the first subset of the first radiology data set being assigned to a first set of cells of the input layer and the first subset of the at least one second radiology data set being assigned to a second set of cells of the input layer, for joint processing of the first subset of the first radiology data set and the first subset of the at least one second radiology data set in the neural network, the first set of cells being different than the second set of cells;

analyzing, via the neural network in a second analyzing step, the second subset of the first radiology data set and the second subset of the at least one second radiology data set, the second subset of the first radiology data set being assigned to the first set of cells of the input layer and the second subset of the at least one second radiology data set being assigned to the second set of cells of the input layer, for joint processing of the second subset of the first radiology data set and the second subset of the at least one second radiology data set in the neural network, the first set of cells being different than the second set of cells; and acquiring the radiological result data on the output layer.

2. The analysis method of claim 1, wherein the neural network includes at least 2 intermediate layers.

3. The analysis method of claim 2, wherein the neural network comprises at least 5 intermediate layers.

4. The analysis method of claim 2, wherein the neural network comprises at least 20 intermediate layers.

5. The analysis method of claim 1, wherein the neural network of the analysis unit is a convolutional network or a Long-Term Short-Term Memory Network.

6. The analysis method of claim 1, wherein at least one of the first radiology data set and the at least one second radiology data set provided, is at least based on X-ray data of two different X-ray energy spectra.

7. The analysis method of claim 1, wherein to provision the first radiology data set and the at least one second radiology data set, a whole X-ray data set is divided, the whole X-ray data set being measured with a third X-ray energy spectrum, the third X-ray energy spectrum including the first X-ray energy spectrum and the second X-ray energy spectrum.

8. The analysis method of claim 7, wherein the whole X-ray data set is at least one of raw data or a reconstructed image data set.

9. A control device, the control device comprising:
one or more processors; and
a system memory storing an executable instruction, when executed, causes the one or more processors to perform the analysis method of claim 1.

10. A non-transitory computer-readable medium storing an executable instruction, when executed, causes a processor to perform the analysis method of claim 1.

11. The analysis method of claim 1, wherein at least one of every single pixel value and every single raw data value of the first radiology data set and the at least one second radiology data set is assigned to a cell of the input layer.

12. The analysis method of claim 1, wherein to provision the first radiology data set and the at least one second radiology data set, a whole X-ray data set is divided, the whole X-ray data set being measured with a third X-ray energy spectrum which includes the first X-ray energy spectrum and the second X-ray energy spectrum by dividing raw data of a measurement with the third X-ray energy spectrum into different raw data sets and reconstructing different image data sets based on the different raw data sets.

13. The analysis method of claim 1, wherein the radiological result data includes at least one of a diagnosis, morphological properties, or quantitative properties.

14. A device for automatically determining radiological result data from radiology data sets, the device comprising:
one or more processors; and
a system memory storing an executable instruction, when executed, causes the one or more processors to
detect, via a data interface, a first radiology data set at least based on X-ray data of a first X-ray energy spectrum and at least one second radiology data set at least based on X-ray data of a second X-ray energy spectrum;
divide the first radiology data set into a first subset and a second subset;
divide the at least one second radiology data set into a first subset and a second subset; and analyze, via a neural network, the first radiology data set and the at least one second radiology data set, the neural network including
an input layer with a plurality of cells, wherein in a first analyzing step the first subset of the first radiology data set is assigned to a first set of cells and the first subset of the at least one second radiology data set is assigned to a second set of cells for joint processing of the first subset of the first radiology data set and the first subset of the at least one second radiology data set, the first set of cells being different than the second set of cells, and in a second analyzing step the second subset of the first radiology data set is assigned to the first set of cells of the input layer and the second subset of the at least one second radiology data set being assigned to the second set of cells of the input layer, for joint processing of the second subset of the first radiology data set and the second subset of the at least one second radiology data set in the neural network, the first set of cells being different than the second set of cells, and wherein a number of the plurality of cells of the input layer are each assigned only one pixel value or only one raw data value of the first radiology data set or the at least one second radiology data set,
a number of intermediate layers, and
an output layer representing the radiological result data, the device being configured to detect the radiological result data on the output layer.

15. The device of claim 14, wherein the device is a control device for controlling an X-ray system.

16. The control device of claim 15, wherein the control device is for controlling a CT system.

17. The device of claim 14, wherein the device is a diagnostic workstation for coupling to an X-ray system.

18. A medical imaging system, the medical imaging system comprising:
an X-ray system; and
the device of claim 14.

19. The medical imaging system of claim 18, wherein the X-ray system includes an energy-resolving detector.

20. The medical imaging system of claim 18, wherein the X-ray system includes a directly converting detector.

21. A non-transitory machine readable medium, storing an executable instruction, when executed, causes a processor to:
divide a first radiology data set into a first subset and a second subset;
divide at least one second radiology data set into a first subset and a second subset; and
analyze, via a neural network, the first subset of the first radiology data set and the first subset of the at least one second radiology data set, the first radiology data set being based on X-ray data of a first X-ray energy spectrum and the at least one second radiology data set being at least based on X-ray data of a second X-ray energy spectrum, the neural network including
an input layer with a plurality of cells, wherein in a first analyzing step the first subset of the first radiology data set is assigned to a first set of cells and the first subset of the at least one second radiology data set is assigned to a second set of cells for joint processing of the first subset of the first radiology data set and the first subset of the at least one second radiology data set, the first set of cells being different than the second set of cells, and in a second analyzing step the second subset of the first radiology data set is assigned to the first set of cells of the input layer and the second subset of the at least one second radiology data set being assigned to the second set of cells of the input layer, for joint processing of the second subset of the first radiology data set and the second subset of the at least one second radiology data set in the neural network, the first set of cells being different than the second set of cells, and wherein a number of the plurality of cells of the input layer are each assigned only one pixel value or only one raw data value of the first radiology data set or the at least one second radiology data set, a number of intermediate layers, and an output layer representing radiological result data, wherein the neural network is configured to generate and make available the radiological result data on the output layer.

\* \* \* \* \*